United States Patent [19]

Stanley et al.

[11] Patent Number: 6,096,869
[45] Date of Patent: *Aug. 1, 2000

[54] TREATMENT OF PAPILLOMAVIRUS-ASSOCIATED LESIONS

[75] Inventors: Margaret Anne Stanley; Cinzia Giuseppina Scarpini, both of Cambridge, United Kingdom

[73] Assignee: Cambridge University Technical Services, Ltd., Cambridge, United Kingdom

[ * ] Notice: This patent issued on a continued prosecution application filed under 37 CFR 1.53(d), and is subject to the twenty year patent term provisions of 35 U.S.C. 154(a)(2).

[21] Appl. No.: 08/621,841

[22] Filed: Mar. 22, 1996

[30] Foreign Application Priority Data

Mar. 22, 1995 [GB] United Kingdom .................. 9505784

[51] Int. Cl.$^7$ .......................... C07K 1/00; A61K 39/00; A61K 39/12; A01N 37/18

[52] U.S. Cl. ................... 530/351; 424/198.1; 424/184.1; 424/204.1; 424/199.1; 514/44; 514/2

[58] Field of Search .............................. 424/198.1, 184.1, 424/204.1, 199.1; 514/44, 2; 530/351

[56] References Cited

U.S. PATENT DOCUMENTS 5,571,515  11/1996  Scott et al. .......................... 424/208.1

FOREIGN PATENT DOCUMENTS

| | | |
|---|---|---|
| 0433827 A2 | 12/1990 | European Pat. Off. . |
| 93/00436 | 6/1992 | WIPO . |
| WO 92/16636 | 10/1992 | WIPO . |
| WO 93/02184 | 2/1993 | WIPO . |
| WO 93/2084 | 10/1993 | WIPO . |

OTHER PUBLICATIONS

Friedmann (1997) Scientific American, Jun. 1997, pp. 96–101.

Verma et al. (1997) Nature, vol. 389, pp. 239–242.

Orkin et al. (Dec. 5, 1995) Report and Recommendations of the Panel to Access the NIH Investment in Research on Gene Therapy. issued by The National Institutes of Health.

Eron, L.J., et al., "Interferon Therapy for Condylomata Acuminata," *The New England Journal of Medicine*, 315(17):1059–1064 (1986).

Chan, S.H., et al., "Induction of Interferon γ Production by Natural Killer Cell Stimulatory Factor: Characterization of the Responder Cells and Synergy with Other Inducers," *J. Exp. Med.*, 173:869–879 (1991).

Afonso, L.C.C., et al., "The Adjuvant Effect of Interleukin–12 in a Vaccine Against *Leishmania major*," *Science*, 263:235–237 (1994).

Martinotti, A., et al., "CD4 T Cells Inhibit in vivo the CD8–mediated Immune Response Against Murine Colon Carcinoma Cells Transduced with Interleukin–12 Genes," *Eur. J. Immunol.*, 25:137–146 (1995).

Scarpini, C.G., et al., "Cytokine mRNA Profiles in Genitoanal Warts," *9th International Congress of Immunology*, Jul. 23–29, 1995. San Francisco: California. 0(0):370 (1995).

Ausbel et al., "Short Protocols in Molecular Biology," 3rd. Edition (John Wiley & Sons), pp. 8–1 to 8–22 (Oct. 1995).

Zou et al., "Structure–Function Analysis of the p35 Subunit of Mouse Interleukin 12*," Journal of Biological Chemistry, 370(11):5864–5871 (Mar. 17, 1995).

Schoenhaut et al., "Cloning and Expression of Murine IL–12," Journal of Immunology, 148(11):3433–3440 (Jun. 1, 1992).

Wolf et al., "Cloning of cDNA for Natural Killer Cell Stimulatory Factor, and Heterodimeric Cytokine with Multiple Biologic Effects on T and Natural Killer cells," Journal of Immunology, 146(9):3074–3081 (May 1, 1991).

Razin et al., "Efficient correction of a mutation by use of chemically synthesized DNA", *Proc. Natl. Acad. Sci. USA*, pp. 4268–4270, (1978).

Gillam et al., "Defined transversion mutations at a specific position in DNA using synthetic oligodeoxyribonucleotides as mutagens", *Nucleic Acids Res.* 6:2973–2985, (1979).

Gillam et al., "Site–Specific Mutagenesis Using Synthetic Oligodeoxyribonucleotide Primers: I", *Gene*, 8:81–97, (1979).

Gillam et al., "Site–Specific Mutagenesis Using Synthetic Ogligodeoxyribonucleotide Primers: II", *Gene* 8:99–106, (1979).

Gillam et al., "Site–Specific Mutagenesis using oligodeoxyribonucleotides: isolation of a phenotypically silent phiX174 mutant, with a specific nucleotide deletion, at very high efficiency", *Gene* 12:129–137, (1980).

Wallace et al., "Directed Deletion of a Yeast Transfer RNA Intervening Sequence", *Science* 209:1396–1400, (1980).

Wallace et al., "Oligonucleotide directed mutagenesis of the human B–globin gene: a general method for producing specific point mutations in cloned DNA", *Nucleic Acids Res.* 9:3647–3656, (1981).

Kudo et al., "Site–specific mutagenesis of cloned DNAs: Generation of mutant of *E. coli* tyrosine suppressor tRNA in which the sequence G–T–T–C corresponding to the universal G–T–Ψ–C sequence of tRNAs is changed to G–A–T–C", *Proc. Natl. Acad. Sci. USA* 78:4753–4757, (1981).

Riggs et al., "Synthetic DNA and Medicine", *Am. J. Hum. Genet.* 31:531–538, (1979).

Simons et al., "Oligonucleotide–directed mutagenesis of gene IX of bacteriophage M13", *Nucleic Acids Res.* 10:821–832, (1982).

Montell et al., "Resolving the functions of overlapping viral genes by site–specific mutagensis at a mRNA splice site", *Nature*, 295:380–384, (1982).

Primary Examiner—Hankyel Park
Attorney, Agent, or Firm—Klarquist Sparkman Campbell Leigh & Whinston, LLP

[57] ABSTRACT

Interleukin-12 (IL-12) or a functional analogue thereof, or a polynucleotide encoding IL-12 or encoding a functional analogue thereof, is used as a therapeutic material or adjuvant in treating papillomavirus-associated lesions e.g. warts due to HPV 6 and/or 11, e.g. condyloma acuminata. IL-12 or a vector encoding it for endogenous production can be used together with a vaccine such as a papillomavirus antigen, or a vector encoding a papillomavirus antigen.

13 Claims, No Drawings

```
                              SEQUENCE LISTING (1) GENERAL INFORMATION:

(iii) NUMBER OF SEQUENCES: 58

(2) INFORMATION FOR SEQ ID NO:1:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:1:

ATGGCCAAAG TTCGAGACAT G                                              21

(2) INFORMATION FOR SEQ ID NO:2:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:2:

TGACTGAAAG TCTATGACCT TTTGGTCCGC ATC                                 33

(2) INFORMATION FOR SEQ ID NO:3:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:3:

ATGGCAGAAG TACCTAAGCT C                                              21

(2) INFORMATION FOR SEQ ID NO:4:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:4:

TGACTCAAGT GGTACGTTAA ACACAGAAGG ATT                                 33

(2) INFORMATION FOR SEQ ID NO:5:

(i) SEQUENCE CHARACTERISTICS:
```

(A) LENGTH: 21 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:5:

ATGTACAGGA TGCAACTCCT G                                              21

(2) INFORMATION FOR SEQ ID NO:6:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:6:

AAAACAGTTT CGTAGTAGAG TTGTGACTGC ACT                                 33

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:7:

ATGAGCCGCC TGCCCGTCCT G                                              21

(2) INFORMATION FOR SEQ ID NO:8:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:8:

GTTGTCTGCT GAAACTCGGA GCGCTAGAA                                      29

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:9:

```
ATGGGTCTCA CCTCCCAACT G                                              21

(2) INFORMATION FOR SEQ ID NO:10:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:10:

TACTCTCTCT TTATAAGTTT CACAAGCTCG ACT                                  33

(2) INFORMATION FOR SEQ ID NO:11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:11:

ATGAGGATGC TTCTGCATTT G                                              21

(2) INFORMATION FOR SEQ ID NO:12:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:12:

CATTACTTGT GGCTCACCTA TTATCTTTCA ACT                                  33

(2) INFORMATION FOR SEQ ID NO:13:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:13:

ATGAACTCCT TCTCCACAAG C                                              21

(2) INFORMATION FOR SEQ ID NO:14:

(i) SEQUENCE CHARACTERISTICS:
        (A) LENGTH: 33 base pairs
        (B) TYPE: nucleic acid
        (C) STRANDEDNESS: single
        (D) TOPOLOGY: linear
```

(iii) HYPOTHETICAL: NO (iv) ANTI-SENSE: NO (xi) SEQUENCE DESCRIPTION: SEQ ID NO:14:

GTCAGGTCGG ACTCCCGAGA AGCCGTTTAC ATC                                              33

(2) INFORMATION FOR SEQ ID NO:15:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (iii) HYPOTHETICAL: NO (iv) ANTI-SENSE: NO (xi) SEQUENCE DESCRIPTION: SEQ ID NO:15:

ATGACTTCCA AGCTGGCCGT G                                                          21

(2) INFORMATION FOR SEQ ID NO:16:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (iii) HYPOTHETICAL: NO (iv) ANTI-SENSE: NO (xi) SEQUENCE DESCRIPTION: SEQ ID NO:16:

CTCTTCAAAA ACTTCTCCCG ACTCTTAAGT ATT                                              33

(2) INFORMATION FOR SEQ ID NO:17:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (iii) HYPOTHETICAL: NO (iv) ANTI-SENSE: NO (xi) SEQUENCE DESCRIPTION: SEQ ID NO:17:

ATGCCCCAAG CTGAGAACCA AGACCCA                                                     27

(2) INFORMATION FOR SEQ ID NO:18:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (iii) HYPOTHETICAL: NO (iv) ANTI-SENSE: NO (xi) SEQUENCE DESCRIPTION: SEQ ID NO:18:

ACCCTATCGA CTGGGTCGGG GAACTCT                                                     27

(2) INFORMATION FOR SEQ ID NO:19:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (iii) HYPOTHETICAL: NO (iv) ANTI-SENSE: NO (xi) SEQUENCE DESCRIPTION: SEQ ID NO:19:

AACTAATGGG AGTTGCCTGG                                           20

(2) INFORMATION FOR SEQ ID NO:20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:20:

GAAGGATTTT TCGCTCCAGG                                           20

(2) INFORMATION FOR SEQ ID NO:21:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:21:

TCACAAAGGA GGCGAGGTTC                                           20

(2) INFORMATION FOR SEQ ID NO:22:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:22:

CAGTACCACC TACGGCAAGT                                           20

(2) INFORMATION FOR SEQ ID NO:23:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:23:

```
ATGAGCACTG AAAGCATGAT C                                                    21
```

(2) INFORMATION FOR SEQ ID NO:24:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:24:

```
CCCGTCCAGA TGAAACCCTA GTAACGGGAC ACT                                       33
```

(2) INFORMATION FOR SEQ ID NO:25:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:25:

```
ATGACACCAC CTGAACGTCT CTTC                                                 24
```

(2) INFORMATION FOR SEQ ID NO:26:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:26:

```
TCATGACAGA AGAAACCTCG GAAGCGAGAC ATC                                       33
```

(2) INFORMATION FOR SEQ ID NO:27:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:27:

```
ATGAAATATA CAAGTTATAT C                                                    21
```

(2) INFORMATION FOR SEQ ID NO:28:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:28:

TACGACAAAG CTCCAGCTTC TCGTAGGGTC ATT            33

(2) INFORMATION FOR SEQ ID NO:29:

(i) SEQUENCE CHARACTERISTICS:
    (A) LENGTH: 29 base pairs
    (B) TYPE: nucleic acid
    (C) STRANDEDNESS: single
    (D) TOPOLOGY: linear (iii) HYPOTHETICAL: NO (iv) ANTI-SENSE: NO (xi) SEQUENCE DESCRIPTION: SEQ ID NO:29:

AACATGATCG TGCGCTCTGC AAGTGCAGC                 29

(2) INFORMATION FOR SEQ ID NO:30:

(i) SEQUENCE CHARACTERISTICS:
    (A) LENGTH: 24 base pairs
    (B) TYPE: nucleic acid
    (C) STRANDEDNESS: single
    (D) TOPOLOGY: linear (iii) HYPOTHETICAL: NO (iv) ANTI-SENSE: NO (xi) SEQUENCE DESCRIPTION: SEQ ID NO:30:

AGGACGGACA GACGTGATAA GGAA                      24

(2) INFORMATION FOR SEQ ID NO:31:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (iii) HYPOTHETICAL: NO (iv) ANTI-SENSE: NO (xi) SEQUENCE DESCRIPTION: SEQ ID NO:31:

GTGGGGCGCC CCAGGCACCA                           20

(2) INFORMATION FOR SEQ ID NO:32:

(i) SEQUENCE CHARACTERISTICS:
    (A) LENGTH: 24 base pairs
    (B) TYPE: nucleic acid
    (C) STRANDEDNESS: single
    (D) TOPOLOGY: linear (iii) HYPOTHETICAL: NO (iv) ANTI-SENSE: NO (xi) SEQUENCE DESCRIPTION: SEQ ID NO:32:

CTTTCGCACG CACTGTAATT CCTC                      24

(2) INFORMATION FOR SEQ ID NO:33:

```
    (i) SEQUENCE CHARACTERISTICS:
        (A) LENGTH: 20 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:33:

ATAGCACGTT TCTCTCTGGC                                             20

(2) INFORMATION FOR SEQ ID NO:34:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:34:

CCTTGTGACG AGAGTCTGTA                                             20

(2) INFORMATION FOR SEQ ID NO:35:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:35:

TGGTGATGAG AGCCACTCAG                                             20

(2) INFORMATION FOR SEQ ID NO:36:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:36:

GTGGCCAAAG TCTTCTGTAC                                             20

(2) INFORMATION FOR SEQ ID NO:37:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (iii) HYPOTHETICAL: NO (iv) ANTI-SENSE: NO
```

(xi) SEQUENCE DESCRIPTION: SEQ ID NO:37:

TTCCGGGTGT CGCCGCTGGA T                                             21

(2) INFORMATION FOR SEQ ID NO:38:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:38:

TGAGGTAGTA CATGAAGTCG                                               20

(2) INFORMATION FOR SEQ ID NO:39:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:39:

TGGTGGCCAC AGCTTGGCAT                                               20

(2) INFORMATION FOR SEQ ID NO:40:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:40:

CTTGCACGAT CGTGTCCTC                                                19

(2) INFORMATION FOR SEQ ID NO:41:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:41:

GCATGTACTA GTTTTGTCAC AAGATTTGGG                                     30

(2) INFORMATION FOR SEQ ID NO:42:

(i) SEQUENCE CHARACTERISTICS:
        (A) LENGTH: 18 base pairs
        (B) TYPE: nucleic acid
        (C) STRANDEDNESS: single (D) TOPOLOGY: linear (iii) HYPOTHETICAL: NO (iv) ANTI-SENSE: NO (xi) SEQUENCE DESCRIPTION: SEQ ID NO:42:

CGTACCCGGG AACCACCT                                                        18

(2) INFORMATION FOR SEQ ID NO:43:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (iii) HYPOTHETICAL: NO (iv) ANTI-SENSE: NO (xi) SEQUENCE DESCRIPTION: SEQ ID NO:43:

CATGGGTGCT TATAAGTCAT C                                                    21

(2) INFORMATION FOR SEQ ID NO:44:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (iii) HYPOTHETICAL: NO (iv) ANTI-SENSE: NO (xi) SEQUENCE DESCRIPTION: SEQ ID NO:44:

CGATCACTGA ACTGCACGCT CCGGG                                                25

(2) INFORMATION FOR SEQ ID NO:45:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (iii) HYPOTHETICAL: NO (iv) ANTI-SENSE: NO (xi) SEQUENCE DESCRIPTION: SEQ ID NO:45:

GCACTTGTCA CAAACAGTGC                                                      20

(2) INFORMATION FOR SEQ ID NO:46:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (iii) HYPOTHETICAL: NO (iv) ANTI-SENSE: NO (xi) SEQUENCE DESCRIPTION: SEQ ID NO:46:

ACACACTTAA AGCAGCCACC                                                      20

(2) INFORMATION FOR SEQ ID NO:47:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:47:

GCGATATCAC CTTACAGGAG                                  20

(2) INFORMATION FOR SEQ ID NO:48:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:48:

TACATAAAAA TCACCAACTG T                                21

(2) INFORMATION FOR SEQ ID NO:49:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:49:

GAGGTATACC TAGAGTACCT C                                21

(2) INFORMATION FOR SEQ ID NO:50:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:50:

TAAAGACATA CTCCAAACTT                                  20

(2) INFORMATION FOR SEQ ID NO:51:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:51:

CAGGTGAAGA ATGCCTTTAA TAAGCTCCAA                                     30

(2) INFORMATION FOR SEQ ID NO:52:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:52:

GAAGAAGTAT GCAGAGCTTG                                                20

(2) INFORMATION FOR SEQ ID NO:53:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:53:

CCAGCAGGTG AAACGTCC                                                  18

(2) INFORMATION FOR SEQ ID NO:54:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:54:

GGCGTGGAGC TGAGAGATAA C                                              21

(2) INFORMATION FOR SEQ ID NO:55:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (iii) HYPOTHETICAL: NO (iv) ANTI-SENSE: NO (xi) SEQUENCE DESCRIPTION: SEQ ID NO:55:

CTACTTCGTC TACTCCCAGG T                                              21

(2) INFORMATION FOR SEQ ID NO:56:

(i) SEQUENCE CHARACTERISTICS:
        (A) LENGTH: 22 base pairs
        (B) TYPE: nucleic acid

```
            (C) STRANDEDNESS: single
            (D) TOPOLOGY: linear (iii) HYPOTHETICAL: NO (iv) ANTI-SENSE: NO (xi) SEQUENCE DESCRIPTION: SEQ ID NO:56:

AGAGTGTGGA GACCATCAAG GA                                              22

(2) INFORMATION FOR SEQ ID NO:57:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (iii) HYPOTHETICAL: NO (iv) ANTI-SENSE: NO (xi) SEQUENCE DESCRIPTION: SEQ ID NO:57:

AATTTAAGGA CACCGTGCCC C                                               21

(2) INFORMATION FOR SEQ ID NO:58:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (iii) HYPOTHETICAL: NO (iv) ANTI-SENSE: NO (xi) SEQUENCE DESCRIPTION: SEQ ID NO:58:

CTGAACCCCA AGGCCAACCG CG                                              22
```

TREATMENT OF PAPILLOMAVIRUS-ASSOCIATED LESIONS

FIELD OF THE INVENTION

This invention relates to materials and methods for treatment of papillomavirus-associated lesions, e.g. HPV-associated lesions such as the tumours designated as genital warts. The invention also relates to methods of producing and using such materials, including immunotherapeutic materials such as vaccines and adjuvants.

BACKGROUND OF THE INVENTION AND PRIOR ART

Many proliferative conditions are known to be associated with papillomaviruses, in particular varieties of warts, such as condyloma acuminata (anogenital warts) and cervical intraepithelial dysplasia and neoplasia, which can develop into cervical cancer.

Condyloma acuminata is caused by infection with human papillomavirus, usually HPV types 6 and 11, and is the most commonly diagnosed viral sexually transmitted disease in the UK. Significant morbidity is associated with the lesions, and available treament regimes are unsatisfactory, with many patients exhibiting recurrent disease. Other HPV types, particularly 16 and 18, are associated with development of intraepithelial dysplasia and neoplasia which may progress to invasive carcinoma tumours of the cervix and (more rarely) of the vulva, vagina or penis. Furthermore, one study showed cervical intraepithelilal neoplasia in 50% of patients with visible genital warts (PG Walker et al, (1983) Br J Ven Dis 59:120–123).

A proportion (about 20%) of patients with condylomata undergo spontaneous regression of their tumours, apparently reflecting an effective immune response mounted by the host. S Aiba et al ((1986) Cancer 58: 1246–1251) reported that tumour regression was characterised by an active cell-mediated immune response in which CD4+ T lymphocytes and macrophages predominate, consistent with a delayed type hypersensitivity response to foreign antigen.

Vaccines have previously been proposed for prophylaxis and therapy of papillomavirus-associated conditions. Thus for example WO 93/00436 (Cancer Research Campaign Technology: WFH Jarrett et al) concerns the use of papillomavirus protein L2, and of related fragments and fusion proteins, for prophylaxis and therapy of papillomavirus-associated conditions; WO 93/20844 (Cancer Research Campaign Technology: M S Campo et al) relates to vaccine uses of papillomavirus E7 protein; and WO 93/02184 (University of Queensland and CLS Ltd: I Frazer et al: Papilloma Virus Vaccine) relates to papillomavirus-like particles comprising L1 protein or L1 and L2 protein and their use as vaccine.

Furthermore WO 96/00583 (Merck: J J Donnelly et al: Polynucleotide Vaccine for Papillomavirus) describes DNA constructs encoding papilloma virus gene products, capable of being expressed upon direct introduction into animal tissues, as prophylactic pharmaceuticals which can provide immune protection against infection by papilloma virus.

In the field of immunology large numbers of cytokines and accessory substances are known, of which one of the known cytokines is now designated IL-12. WO 92/05256 (Genetics Institute and Wistar Institute: G Trinchieri et al: Natural Killer Stimulatory Factor) describes IL-12 as a human cytokine under the designation natural killer stimulatory factor. WO 92/05256 contains a recommendation, in general terms, to use NKSF or one or both of its subunits or peptide fragments thereof in a suitable pharmaceutical carrier, in "methods for treating cancer, viral infections such as AIDS, bacterial infections and other disease states responsive to the enhanced presence of gamma interferon or GM-CSF production".

EP 0 433 827 (Hoffmann-la Roche: RA Chizzonite et al: Cytotoxic lymphocyte maturation factor and monoclonal antibodies directed thereto) describes IL12 under the designation cytotoxic lymphocyte maturation factor (CLMF). IL-12 has been alternatively designated as natural killer cell stimulatory factor.

Reference in connection with IL-12 is also made to M Kobayashi et al. J Exp Med (Sep 1989) 170(3) 827–845 "Identification and purification of natural killer cell stimulatory factor (NKSF), a cytokine with multiple biologic effects on human lymphocytes"; to A S Stern et al, Proc Nat Acad Sci USA (Sep 1990) 87:6808–6812, "Purification to homogeneity and partial characterization of cytotoxic lymphocyte maturation factor from human B-lymphoblastoid cells"; and to S F Wolf et al. J Immunol (May 1991) 146(9):3074–3081, "Cloning of cDNA for natural killer cell stimulatory factor, a heterodimeric cytokine with multiple biologic effects on T and natural killer cells". IL-12 occurs as a heterodimer of two covalently linked polypeptide chains, p40 and p35, the products of distinct genes. IL-12 has been reported as produced by monocytes/macrophages, B cells, mast cells and by NK cells. An IL-12 receptor has been found on activated T cells and activated NK cells, and is a single transmembrane glycoprotein of 70–75 kDa. IL-12 has been reported to promote the growth of activated NK, CD4+ and CD8+ T cell subsets and to increase both antibody dependent cellular cytotoxicity and NK mediated cytotoxicity. IL-12 is also an inducer of interferon-gama (IFN-gamma) which can activate macrophages.

A report of injecting interferon-gamma (one of the cytokines) into genital warts has been made (L J Eron et al, (1986) New Engl J Med vol 315(17); and L Belli et al (Condylomata International Study Group), (1991) J Amer Med Ass, vol 265(20) (May 22/29).).

The prior art leaves it still desirable to seek further treatments for papillomavirus-associated conditions and for the tumours to which these can give rise.

SUMMARY AND DESCRIPTION OF THE INVENTION

The present invention arises from a surprising finding that IL-12 is present in 100% of regressing HPV-induced tumours surveyed by the present inventors in a clinical study—unlike many other cytokines also surveyed.

Given the association between the presence of IL-12 in lesions resulting from HPV infection and regression of these lesions, the present invention therefore provides various aspects concerned generally with therapy of papillomavirus-associated lesions, e.g. treatment of tumours. The conditions to which the invention is applicable include any papillomavirus infection, and in particular include any epithelial cell proliferation induced as a consequence of infection with a human or non-human animal papillomavirus including benign warts or cutaneous or mucosal surfaces including skin, cervix, vagina, vulval, anus, rectum, penis. meatus, urethra, larynx, oropharynx, buccal cavity, tongue, and nasopharynx. The invention is also applicable to malignant lesions associated with papillomavirus infection such as anogenital cancers including cervix, vulva, anus, penis; and cutaneous, laryngeal and oesophageal cancers. Of particular interest is the treatment of anogenital warts such as those caused by HPV types 6 and 11.

According to the present invention, therefore, the cytokine interleukin-12, (IL-12) and functional analogues thereof, are provided for use as therapeutic materials or as adjuvants in the treatment of papillomavirus-associated lesions.

Such lesions can be for example warts caused by HPV type 6 and/or type 11, such as genital warts, also known as anogenital warts, or condyloma acuminata.

Also provided by the present invention as therapeutic materials or as adjuvants in the treatment of papillomavirus-associated lesions, are polynucleotides encoding IL-12 or encoding functional analogues thereof.

Aim of treatments according to embodiments of the invention is to increase the amount of IL-12 in an individual, especially for example at a tissue location where immune response to papillomavirus can have therapeutic effect, e.g. at or in the neighbourhood of a lesion associated with HPV.

According to the invention, IL-12 itself can be administered to an individual with an HPV-associated lesion for treatment of the lesion.

Alternatively, according to certain examples of the invention, an inducer of IL12 (e.g. in the form of a polynucleotide, e.g. carried by a recombinant virus vector encoding IL-12 and able to cause expression of the encoded IL-12 when it infects a cell) can be administered to an individual with an HPV-associated lesion for treatment of the lesion. Generally such an inducer can be a material, e.g. a molecular species, able to induce a local or systemic increase in the level of IL-12, e.g. as a result of increased endogenous production or release of IL-12 by cells.

Thus, according to the invention, pharmaceutical compositions for use in the treatment of papillomavirus-associated conditions such as tumours can comprise IL-12 or an inducer thereof; and IL-12 and inducers thereof can be used in methods for the manufacture of medicaments, compositions for use in therapy of papillomavirus-associated conditions, e.g. in anti-tumour treatment.

The IL-12 or inducers thereof can be present in admixture together with further component(s) as described below.

Thus the invention provides in one aspect a pharmaceutical treatment material comprising IL-12, or a functional analogue thereof, for use as an immunotherapeutic or as a vaccine adjuvant; e.g. for use in treatment of papillomavirus-associated tumours.

The pharmaceutical treatment material can comprise in combination (i) IL-12, or a functional analogue thereof, for use as a vaccine adjuvant, and (ii) a papillomavirus antigen, or a vector encoding and able to cause expression of a papillomavirus antigen, for use as a vaccine.

Component (ii) can comprise at least one papillomavirus protein or antigenic fragment or fusion protein corresponding thereto: e.g. a polypeptide with at least a substantial part of the sequence of at least one of proteins E1, E2, E4, E5, E6, E7, L1, and/or L2 of HPV 6, 11, 16 and/or 18. Generally in the invention the corresponding proteins and antigens of HPV types 31, 31, 35, 45, 51, 52 and 56 are also applicable, particularly for example in connection with papillomavirus lesions associated with cervical intraepithelial neoplasia or the risk thereof.

Alternatively component (ii) can Comprise a recombinant virus vector encoding and able to cause expression of at least one papillomavirus protein or antigenic fragment or fusion protein corresponding thereto. Such a vector can comprise at least one recombinant vaccinia virus encoding a polypeptide with at least a substantial part of the sequence of at least one papillomavirus protein E1, E2, E4, E5, E6, E7, L1, and/or L2 of HPV 6, 11, 16 and/or 18.

Alternatively, as stated above, inducers of IL-12 can be used. The present invention can in certain embodiments include the use of polynucleotides encoding one or both subunits (chains) of IL-12 such as the p40 subunit together with the p35 subunit of IL-12, or in certain cases encoding the p40 subunit alone, and other functional analogues thereof, as therapeutic materials or as an adjuvant in the treatment of papillomavirus-associated lesions.

This can be useful for example in connection with tissues such as keratinocytes which are capable of constitutively expressing the p35 chain but not the p40 chain of the heterodimer IL-12 (G Muller et al 1994, J Clin Invest 94:1799–1805). IL-12 activity has been reported to depend in normal consitions in vivo on a heterodimeric form involving a p40 subunit (ML Kobayashi et al 1989 J Exp Med 170:827–832: S F Wolf et al, 1991, J Immunol 146:3074–3081).

Thus, for example, in further aspects the invention provides pharmaceutical treatment material comprising a polynucleotide encoding and able to cause expression of IL-12, or its p40 subunit, or other functional analogue thereof, for use as an immunotherapeutic or as a vaccine adjuvant.

The polynucleotide can form part of a recombinant virus vector, e.g. a genetically disabled herpesvirus vector (for which reference is made to WO 92/05263 and WO 94/21807 (Immunology Ltd/Cantab Pharmaceuticals: Inglis et al), and WO 92/16636 (Immunology Ltd: Boursnell et al)). In this connection, the virus vector can for example comprise a mutant HSV1 or HSV2 having a deletion in the gH gene, and carrying (at the locus of deletion of gH) an inserted heterologous gene or genes encoding IL-12, or its p40 subunit, or other functional analogue thereof. Alternatively, plasmid DNA or a more complex vector can be used, e.g. with suitable regulatory sequences for expression in eukaryotic cells.

Such a polynucleotide encoding and able to cause expression of IL-12, or a functional analogue thereof, can be used as a vaccine adjuvant, in combination with a papillomavirus antigen, or a vector encoding and able to cause expression of a papillomavirus antigen, for use as a vaccine. Examples of such vaccine elements can be as already stated above.

If desired, the polynucleotide encoding the IL-12 or analogue can be encoded and carried by the same vector that encodes the papillomavirus antigen, and can be encoded either as separate proteins or as a fusion protein e.g. containing HPV-derived aminoacid sequence, and aminoacid sequence from one or other or both of the IL-12 chains.

Endogenous production of IL-12 can also be induced in a treated subject by a local or distally administered stimulus such as an adjuvant, along with any other desired treatment e.g. a vaccine.

Treatment methods according to the invention include treatments to increase the level of IL-12 in or around a papillomavirus-associated lesion such as a tumour by administration of a pharmaceutical according to the invention in the vicinity of the lesion, e.g. in the case of an external or accessible tumour of skin or mucosa.

IL-12 protein can be sole active ingredient in a pharmaceutical composition according to the invention: e.g. as biologically active heterodimeric IL-12 protein administered per se locally at or near a lesion site or systemically: local administration is preferred. Alternatively, further active ingredients such as vaccines can be given. Vaccines that can be used alongside the IL-12 or inducer thereof include killed HPV preparations, or killed or live vectors such as vaccinia virus vector, carrying nucleic acid encoding HPV protein(s) or antigen(s); or corresponding 'naked DNA'. Suitable HPV proteins to encode include those mentioned elsewhere herein.

Pharmaceutical compositions according to examples of the present invention can be formulated to be given e.g. orally, or by injection, which can be cutaneous, subcutaneous, intravenous, intramuscular or intradermal.

Pharmaceutical compositions according to examples of the present invention can comprise, in addition to the respective active ingredient, pharmaceutically acceptable vehicles, excipients, carriers, other adjuvants, buffers, stabilisers and other per-se known materials, preferably non-toxic and free from incompatibility with the chosen active ingredients. Those pharmaceutical compositions which are for topical administration can comprise creams and emulsions. Where proteins are given they can be given e.g. in aqueous buffer or in known slow release form such as liposomes and microparticles. Oral compositions can be given as tablets or capsules e.g. comprising gelatin, or as powders or liquids. Liquid compositions can comprise water, e.g. as physiological saline or dextrose or other saccharide solution, glycerin or other glycols, ethylene or propylene glucols or polyethylene glycol; petroleum; animal, vegetable, mineral or synthetic oils.

Pharmaceutical compositions for injection can comprise per-se known sterile injectable vehicles, often pyrogen-free, with suitable pH, isotonicity and stability, e.g. isotonic vehicles such as sodium chloride injection, Ringer's injection, and lactated Ringer's injection. Suitable examples of vehicles for giving IL-12 by injection can comprise buffer, human serum albumin and glycine, or human serum albumin and saline for injection (see L J Eron et al (1986) New Engl J Med, vol 315(17); and L Belli et al (Condylomata International Study Group). (1991), J Amer Med Ass, vol 265(20) (May 22/29)).

Therapeutically effective amounts of the materials provided for use according to the present invention can be as mentioned below or can be as readily determined by quantitative assessment of tumours e.g. as tumour area or volume.

Alternatively, dosage and progress of treatment can be assessed by biopsy of the lesions and assessment of the levels or the expression of IL-12 present therein, by immunoassay or other immunochemical determination (as can be readily adapted from per-se well known imunoassay or immunochemical methods by using antibody of appropriate binding specificity for IL-12); or by PCR methods, for example as described below.

Dosages of active ingredient can thus be as mentioned herein or as otherwise adjusted by a prescribing physician according to the location, type and severity of lesions in a clinical case under treatment and the indications provided by such assay methods.

Protein IL-12 can be injected as sole active ingredient in the range 1 pg to 1 mg per dose, e.g. in the range 10 pg to 10 micro-g per dose. e.g. in the range 10 pg to 1 micro-g per dose. When used as a vaccine adjuvant the dose can for example be in the range 1 pg to 10 micro-g per dose, e.g. 100 pg to 1 micro-g per dose.

In the use of DNA encoding IL-12, the dose can be for example 1 ng to 1 mg per dose, e.g. 100 ng to 100 micro-g per dose.

The treatments described herein can be combined with other forms of treatment, e.g. administration of anti-tumour compositions and/or other cytolytic or cytodestructive treatment, including surgical excision, cryosurgery, electrocauterisation, laser therapy and application of podophyllum resin. The different treatments can be simultaneous or sequential.

The invention Is further described for illustration and not by way of limitation by reference to the following examples and associated test methods:

USE OF IL-12 AS AN IMMUNOTHERAPEUTIC FOR HPV TUMOURS:

For this use, recombinant IL-12 can be produced in-vitro by expression of both the p35 and p40 chains of IL-12 in a suitable expression system, preferably a mammalian cell expression system but alternatively in a yeast or baculovirus expression system. Such expression systems are well known in the art of rDNA technology and known cloning and expression vectors and other relevant materials con be readily adapted to the expression of IL-12. WO 92/05256 (Genetics Institute and Wistar Institute: G Trinchieri et al: Natural Killer Stimulatory Factor) describes IL-12 as a human cytokine under the designation natural killer stimulatory factor, and describes methods for producing it and pharmaceutical preparations containing it. EP 0 433 827 (Hoffmann-la Roche: RA Chizzonite et al: Cytotoxic lymphocyte maturation factor and monoclonal antibodies directed thereto) describes IL12 under the designation cytotoxic lymphocyte maturation factor (CLMF) and describes its production and synthesis by a human B-lymphoblastoid cell line.

IL-12 so produced can be purified by per-se standard techniques, e.g. as described in WO 92/05256 (Genetics Institute and Wistar Institute: G Trinchieri et al) and EP 0 433 827 (Hoffmann-la Roche: RA Chizzonite et al) and other references noted above.

Recombinant IL-12 preparations can be used to treat genital warts, and can be formulated with pharmaceutically acceptable carriers, for example as aqueous solutions, or as encapulated forms e.g. in biodegradable microparticles or liposomes, or in aqueous cream formulations of the protein.

Applied topically, e.g. directly to the HPV wart or other lesion, IL-12 can be applied for example in a dose range of 0.01–1000 microgram/day.

Pharmaceutical formulations of IL-12 for this purpose can be topical preparations or parenteral, especially injectable, preparations.

USE OF IL-12 AS AN ADJUVANT TO AN HPV VACCINE:

IL-12 can also be used to treat HPV disease by use as a vaccine adjuvant.

HPV vaccines to which IL-12 can be added as an adjuvant include recombinant HPV proteins, fusion proteins, fragments, or peptides: for example those described in WO 93/00436 (Cancer Research Campaign Technology: WFH Jarrett et al) which concerns the use of papillomavirus protein L2, and of related fragments and fusion proteins, for prophylaxis and therapy of papillomavirus-associated conditions.

Such vaccines can be combined with another adjuvant such as alumininum hyrdroxide gel e.g. in the form of a preparation known as Alhydrogel (TM), and with per-se known biodegradable microparticles or liposomes.

Alternative forms of HPV vaccines with which IL-12 can be combined include recombinant virus-like particles, e.g. as described in WO 93/02184 (University of Queensland and CLS Ltd: I Frazer et al: Papilloma Virus Vaccine).

Alternatively nucleic acid based plasmid vaccines, e.g. as described in WO 96/00583 (Merck: J J Donnelly et al:

Polynucleotide Vaccine for Papillomavirus) can be used in conjunction with IL-12 or polynucleotide encoding it.

Alternatively, recombinant vectors such as vaccinia virus vectors, e.g. those carrying genes encoding HPV proteins or related fusion proteins, e.g. as described in WO 92/16636, can be used. WO 92/16636 (Immunology Ltd: MEG Boursnell et al: Recombinant Virus Vectors Encoding Human Papillomavirus Proteins) describes for example recombinant virus vectors encoding part or all of HPV wild-type proteins such as HPV16E7 and HPV18E7 or mutant proteins immunologically cross-reactive therewith.

The recombinant IL-12 used as an HPV vaccine adjuvant can be a mixture of IL-12 and vaccine administered at the same site. Alternatively it can be used as individual components in a combination treatment in which the components are administered individually, e.g. at the same site and time, or at different sites and/or times. For example. IL-12 can be administered topically while a vaccine is given systemically by injection. For example IL-12 administration can be on a daily basis, e.g. for a week from day 0, while injection of vaccine can be on a periodical basis, e.g. at day 0, day 14 and day 28.

DELIVERY OF IL-12 BY MEANS OF cDNA:

IL-12 can be used in the treatment of HPV disease by delivering a polynucleotide such as a cDNA encoding IL-12.

This can be given for example in the form of: naked plasmid DNA encoding both chains of IL-12. They can be encoded as separate proteins on the same plasmid either under the control of separate promoters, which can be similar or different, or under the control of a single promoter.

Alternatively cDNAs encoding the two chains can be fused together to produce a cDNA coding for a single fusion protein, which cain if desired have a peptide spacer located between the sequences corresponding to the two IL-12 subunits.

Alternatively the two chains of IL-12 can be encoded on separate plasmids. The two plasmids can be given as a mixture at one or more injection sites, or the plasmids can be injected separately into different injection sites.

Alternatively, a polynucleotide encoding only the p40 subunit of IL-12 can be given: especially where the polynucleotide is to be used to cause expression in cells such as keratinocytes where the other subunit. p35, is constitutively expressed.

The polynucleotide such as cDNA encoding either the p40 and p35 subunits or the p40 subunit of IL-12 can be delivered by a vector such as a recombinant viral or bacterial vector. A usable viral vector can be a recombinant vector based on a retrovirus, an adenovirus, an adeno-associated virus a herpesvirus, poxvirus or other virus. The virus can be replication competent, e.g. an attenuated live virus, or it can be a replication-defective virus, e.g. one that is unable to generate infectious new virus particles in the vaccinated subject owing to a genetic defect in the virus, by deletion of an essential viral gene. Alternatively the virus-related vector can be an amplicon associated with a helper virus.

Usable bacterial vector systems include *Lactococcus lactis*, attenuated Salmonella and other safe bacterial systems.

The IL-12 chains can be encoded as separate proteins in the same virus or bacterium either under the control of separate promoters, which can be similar or different, or under the control of a single promoter. Alternatively, cDNAs encoding the two chains can be fused and made to encode a single fusion protein, as mentioned above. Alternatively the two chains can be encoded in separate vectors.

IL-12 cDNA can also be delivered by liposome delivery.

Administration of naken plasmid DNA can be achieved by injection of an aqueous solution containing the the plasmid DNA. Generally, route of injection of the materials provided hereby can be intramuscular, subcutaneous or intradermal route, e.g. directly into or adjacent to a HPV-associated lesion (tumour, wart).

Alternative usable sites of injection are: skin or mucosa immediately adjacent to an HPV-associated lesion, and skin or mucosal sites further distant from the HPV-associated lesions.

Another recently described delivery method can be applied, by adsorbing the DNA on gold particles and injecting the particles by a gun.

Administration of viral- or bacterial-based vectors can be by injection of a composition, e.g. aqueous composition containing the modified virus or bacterium, by intramuscular, subcutaneous or intradermal route, e.g. directly into a HPV-associated lesion or if not at the site of the lesion then immediately adjacent to the lesion or at a distant site. The vector can alternatively be given at a mucosal surface by intranasal, oral or other administration.

The IL-12 polynucleotide such as cDNA or vector containing such a polynucleotide can be used as a vaccine adjuvant for the treatment of HPV-induced disease.

The associated vaccine can comprise for example a naked plasmid DNA encoding one or more HPV-associated antigens, which can be one or more of the gene products derived from a HPV genome expressed either individually or in the form of a fusion protein. DNA encoding the HPV antigen can be on the same plasmid as the the IL-12 gene or on a separate plasmid.

Alternatively IL-12-encoding polynucleotide can he given in association with HPV-antigen-encoding polynucleotide delivered in a viral or bacterial vector(s) as described above or via liposome delivery. The IL-12 and the HPV antigen(s) can be encoded in the same vector or in separate vectors.

DNA encoding IL-12 chains can code for two separate proteins which associate to form a biologically active molecule or can code for a fusion protein containing sequences of both chains of the IL-12, optionally separated by a spacer aminoacid sequence.

TEST METHODS

The following test methods were used in the inventors' clinical study mentioned above and further described below, and are also, applicable to monitoring during the course of treatments according to the present invention.

Cytokine mRNA Analysis of Tumour Cells:

Tumours analysed here were genital warts from patients with condyloma acuminata. As discussed, these are caused by HPV infection, Sampling of the Genital Lesions:

The genital lesions utilised in this study were taken at the Department of Genito-Urinary Medicine, Jefferiss Wing, St Mary's Hospital, Paddington, London. In all cases lesions were treated with Betadine (TM) for the 24 hours prior to sampling. Lesions were resected and immediately snap frozen in liquid nitrogen. Samples were then kept at −70 deg.C until analysed.

RNA Extraction from the Biopsies:

RNA was extracted from the samples using RNAzol B (from Cambio, Cambridge, UK), a commercial product based on the method of P Chomczynski et al (1987) Anal Biochem 162:156–161. Frozen tissue was put in a tube containing at least 1 ml of RNAzol B on ice and homogenised with an electric homogeniser (from OMNI International 1000, Camlab, Cambridge UK). The resultant suspension was transferred to 1.5 ml autoclaved eppendorf tubes and 0.2 ml chloroform was added to each 2 ml of homogenate. Samples were vigorously shaken for 15 seconds and the suspension was left on ice for at least 15 minutes, then tubes were centrifuged at 12,000 g for 15 min at 4 deg.C. The samples divided into two phases, an upper aqueous phase and a lower organic phase. The upper phase was transferred to a new tube and an equal volume of isopropanol was added.

To precipitate the RNA, samples were stored at −20 deg.C for at least 16 hours, then centrifuged for 15 minutes at 12,000 g at 4 deg.C. The supernatant was removed and the pellet washed with 70% ethanol. The RNA was briefly dried under vacuum, resuspended in 50–100 micro-l of DEPC-treated water and quantitated by reading at 260 nm on a spectrophotometer. Small aliquots of the RNA were then stored at −70 deg.C.

Checking Quality of the RNA Extracted from the Biopsies:

To verify that the RNA extracted from the samples was not degraded, small aliquots were run on an agarose gel containing 6.6% formaldehyde with markers for RNA 18 S and 28 S. The RNA was visualised by staining with ethidium bromide (0.5 micro-g/ml) in ammonium acetate 0.1M for 30–60 minutes. When the bands corresponding to rRNA 18 S and 28 S were visible the gel was photographed and only the samples which showed clear bands for the ribosomal RNA were used for further study.

Enzymatic Amplification of RNA with RT-PCR:

(a) Synthesis of DNA Utilising the RNA as Template:

2 micro-g of total RNA extracted from the genital lesions was used as template for reverse transcription. The RNA with 500 ng of poly(T)18 primer in a final volume of 20 micro-l was incubated at 65 deg.C for 15 minutes then chilled on ice. The following mixture was prepared for each sample:

10 micro-l of 5×Reverse Transcriptase Buffer 2 micro-l DTT 0.1M (dithiothreitol)

5 micro-l 4dNTP mix 8 mM (2 mM each)

2 micro-l (20 U) RNAsin 10 micro-l water.

The 29 micro-l of this mix were added to the tube containing the RNA. 1 micro-l (200 U) of Superscript (TM) Reverse Transcript se was added to each sample and the tubes were incubated for 1 hour at 42 deg.C. At the end of this incubation 15 micro-l of Tris-Cl 10 mM, EDTA 10 mM. pH 7.5 were added, then 200 micro-l of buffered phenol was added, samples briefly vortexed and centrifuged for 5 minutes at high speed, room temperature. The upper aqueous phase was transferred to a new tube, then 200 micro-l of chloroform:isoamyl alcohol 24:1 were added. After vortexing and spinning at high speed, room temperature, the upper phase was transferred to a new tube, to which 20 micro-l of sodium acetate 3M and 500 micro-l of absolute alcohol were added. Samples were stored at −20 deg.C overnight or at −70 deg.C for 15 minutes, then centrifuged for 15 minutes at high speed, 4 deg.C. The supernatant was removed and the pellet briefly dried under vacuum and resuspended in 100 micro-l of water. The cDNA obtained was stored at −20 deg.C.

(b) Amplification of cDNA with Specific Primers:

5 micro-l of the cDNA obtained by reverse transcription were utilised to amplify specific sequences of cytokines. The primers utilised for PCR amplification were as follows:

IL-1-alpha 5' ATGGCCAAAGTTCGAGACATG SEQ ID NO:1

IL-1-alpha 3' CTACGCCTGGTTTTCCAGTATCT-GAAAGTCAGT SEQ ID NO:2

IL-1-beta 5' ATGGCAGAAGTACCTAAGCTC SEQ ID NO:3

IL-1-beta 3' TTAGGAAGACACAAATTGCATGGT-GAACTCAGT SEQ ID NO:4

IL-2 5' ATGTACAGGATGCAACTCCTG SEQ ID NO:5

IL-2 3' TCACGTCAGTGTTGAGATGATGTTTGA-CAAAA SEQ ID NO:6

IL-3 5' ATGAGCCGCCTGCCCGTCCTG SEQ ID NO:7

IL-3 3' AAGATCGCGAGGCTCAAAGTCGTCGTTG SEQ ID NO:8

IL-4 5' ATGGGTCTCACCTCCCAACTG SEQ ID NO:9

IL-4 3' TCACGTGAACACTTTGAATATTTCTCTCTCAT SEQ ID NO:10

IL-5 5' ATGAGGATGCTTCTGCATTTG SEQ ID NO:11

IL-5 3' TCAACTTTCTATTATCCACTCGGTGT-TCATTAC SEQ ID NO:12

IL-6 5' ATGAACTCCTTCTCCACAAGC SEQ ID NO:13

IL-6 3' CTACATTTGCCGAAGAGCCCTCAGGCTG-GACTG SEQ ID NO:14

IL-8 5' ATGACTTCCAAGCTGGCCGTG SEQ ID NO:15

IL-8 3' TTATGAATTCTCAGCCCTCTTAAAAACTTCTC SEQ ID NO:16

IL-10 5' ATGCCCCAAGCTGAGAACCAAGACCCA SEQ ID NO:17

IL-10 3 TCTCAGGGGCTGGGTCAGCTATCCCA SEQ ID NO:18

IL-12 p35 5' AACTAATGGGAGTTGCCTGG SEQ ID NO:19

IL-12 p35 3' GGACCTCGCTTTTTAGGAAG SEQ ID NO:20

IL-12 p40 5' TCACAAAGGAGGCGAGGTTC SEQ ID NO:21

IL-12 p40 3' TGAACGGCATCCACCATGAC SEQ ID NO:22

TNF-alpha 5' ATGAGCACTGAAAGCATGATC SEQ ID NO:23

TNF-alpha 3' TCACAGGGCAATGATCCCAAAGTA-GACCTGCCC SEQ ID NO:24

TNF-beta 5' ATGACACCACCTGAACGTCTCTTC SEQ ID NO:25

TNF-beta 3' CTACAGAGCGAAGGCTCCAAAGAAGA-CAGTACT SEQ ID NO:26

IFN-gamma 5' ATGAAATATACAAGTTATATC SEQ ID NO:27

IFN-gamma 3' TTACTGGGATGCTCTTCGACCTC-GAAACAGCAT SEQ ID NO:28

TGF-beta1 5' AACATGATCGTGCGCTCTGCAAGTG-CAGC SEQ ID NO:29

TGF-beta1 3' AAGGAATAGTGCAGACAGGCAGGA SEQ ID NO:30

Actin 5' GTGGGGCGCCCCAGGCACCA SEQ ID NO:31

Actin 3' CTCCTTAATGTCACGCACGCTTTC SEQ ID NO:32

CD3delta 5' ATAGCACGTTTCTCTCTGGC SEQ ID NO:33

CD3delta 3' ATGTCTGAGAGCAGTGTTCC SEQ ID NO:34

CD4 5' TGGTGATGAGAGCCACTCAG SEQ ID NO:35

CD4 3' CATGTCTTCTGAAACCGGTG SEQ ID NO:36

CD8 5' TTCCGGGTGTCGCCGCTGGAT SEQ ID NO:37

CD8 3' GCTGAGTACATGATGGAGT SEQ ID NO:38 c-fms 5' TGGTGGCCACAGCTTGGCAT SEQ ID NO:39 c-fms 3' CTCCTGTGCTAGCACGTC SEQ ID NO:40

IgG 5' GCATGTACTAGTTTTGTCACAAGATTTGGG (SEQ ID NO:41)
IgG 3' TCCACCAAGGGCCCATGC (SEQ ID NO:42)
The following mix was prepared for each sample:
- 2.5 micro-l 20×React Buffer
- 3 micro-l MgCl2 25 mM
- 1 micro-l 4dNTP mix 40 mM (10 mM each)
- 2.5 micro-l each primer
- 31.5 micro-l water 43 micro-l of the mix were transferred to a 0.5 ml eppendorf tube and 5 micro-l of the template cDNA were added. 2 micro-l of thermostable DNA polymerase Tfl (from Cambio, Cambridge UK) was then added. The mixture was then overlaid with 20 micro-l of mineral oil and amplified for 60 cycles at the following temperatures: denaturation: 94 deg.C for 1 minute; annealing: 55 deg.C for 1 minute; elongation: 72 deg.C for 2 minutes.

The amplification was preceded by a prolonged period of denaturation at 94 deg.C for 5 minutes and followed by a cycle at 72 deg.C for 10 minutes, to eliminate the remaining activity of the polymerase.

The presence of the appropriate band was verified by running 20 micro-l of the PCR product on a 1.5% agarose gel containing ethidium bromide. When the gel had been run for an adequate length of time, it was photographed and utilised to transfer the DNA to a nitrocellulose membrane. The gel was denatured for two cycles of 20 minutes each in NaOH 0.5M. NaCl 1M, then washed in water and neutralised in Tris-Cl 0.5M, pH 7.4. NaCl 3M for two cycles of 20 minutes. The gel was transferr3ed overnight to a nitrocellulose membrane in SSC 20× utilising Quickdraw blotting paper (from Sigma International). The membrane was then equilibrated with SSC 20×, air dried and baked for 2 hours at 80 deg.C, then stored at 4 deg.C until used.

(c) Confirmation of the Identity of the PCR Product:

To confirm the identity of the PCR product the membrane was hybridised with digoxigenin labelled probes that recognise internal sequences of the cytokine amplified by PCR, following the protocol by Boehringer Mannheim in their in-situ hybridisation guide. Internal probes used for hybridization with PCR products were as follows:

IL-1-alpha CATGGGTGCTRATAAGTCATC (SEQ ID NO:43)
IL- 1beta CGATCACTGAACTGCACGCTCCGGG (SEQ ID NO:44)
IL-2 GCACTTGTCACAAACAGTGC (SEQ ID NO:45)
IL-3 ACACACTTAGCAGCCACC SEQ ID NO:46
IL-4 GCGATATCACCTTACAGGAG SEQ ID NO:47
IL- 5 TACATAAAAATCACCAACTGT SEQ ID NO:48
IL-6 GAGGTATACCTAGAGTACCTC SEQ ID NO:49
IL-8 TAAAGACATACTCCAAACTT SEQ ID NO:50
IL-10 CAGGTGAAGAATGCCTTTAATAAGCTCCAA SEQ ID NO:51
IL-12 p35 GAAGAAGTATGCAGAGCTTG SEQ ID NO:52
IL-12 p40 CCAGCAGGTGAAACGTCC SEQ ID NO:53
TNF-alpha GGCGTGGAGCTGAGAGATAAC SEQ ID NO:54
TNF-beta CTATTCGTCTACTCCCAGGT SEQ ID NO:55
IFN-gama AGAGTGTGGAGACCATCAAGA SEQ ID NO:56
TGF-beta1 AATTAAGGACACCGTGCCCC SEQ ID NO:57
beta-actin CTGAACCCCAAGGCCAACCGCG SEQ ID NO:58

Membranes were prehybridised in at least 20 ml/100 sq cm of N-lauroyl sarcosine 0.1% v/v. SDS 0.02% v/v and Blocking Reagent for nucleic acid hybridisation (Boehringer Mannheim) 1%, for 1 hour at 37 deg.C. The hybridisation was performed for 4 hours with 10 pmol/ml of oligonucleotide in 4 ml/100 sq cm of hybridisation buffer at 37 deg.C. Membranes were then washed twice at room temperature with SSC 2×, SDS 0.1% v/v, 5 minutes per wash, followed by 2 washes of 15 minutes each at 37 deg.C with SSC0.1×, SDS 0.1% v/v. Membranes were equilibrated in Buffer 1 (Maleic acid 100 mM, NaCl 150 mM. pH 7.5) for a few minutes, then incubated in Blocking Reagent 1% for 30 minutes. Membranes were then incubated with anti-DIG antibody conjugated with alkaline phosphatase (Boehringer Mannheim) diluted 1:5000 for 30 minutes at room temperature under gentle shaking. Membranes were washed twice for 5 minutes with Buffer 1 and then transferred briefly to Buffer 3 (Tris-Cl 100 mM, pH 9.5. NaCl 100 mM, MgCl2 50 mM). Membranes were then incubated with colour change solution (45 micro-l NBT. 35 micro-l X-phosphate in 10 ml Buffer 3) for 16 hours, when the reaction was blocked by washing in Buffer 1. The visualization of the correct size band in both the positive control and the sample indicated specificity of the amplified cDNA.

Results:

The results of the RT-PCR analysis in the clinical study are given in the attached tables a to e of the accompanying drawings. The division into different tables was based on similarity in the pattern of cytokine expression in regressing or non-regressing warts. Table a relates to cases of non-regressing warts with no evidence of IL-2 p40 or IFN-gamma transcription. Table b relates to cases of non-regressing warts with no evidence of IL-12 p40 transcription but with evidence of IFN-gamma transcription. Table c relates to cases of non-regressing warts with evidence of IL-12 p40 transcription. Table d relates to cases of regressing warts.

The intensity of the signals was determined by comparison between samples amplified in the same reaction and then normalised by comparison to the intensity of the actin band.

In the study, the inventors also analysed normal cervical tissue in order to have data on gene expression in normal tissue. Those samples were from uterus which had been removed for reasons not related to HPV infection and were snap frozen as the other samples.

All lesions showed transcripts for IL-1beta, IL-8, IL-12 p35 and TGF-beta1, although at different levels. No wart sample was positive for IL-3, IL-4 or IL-10. IL-4 was seen only once in a normal cervical tissue (NCx2). Two samples were positive for IL-6, whereas transcripts for IL-5 were seen in five samples.

Non-regressing lesions are grouped in Table a and did not show transcripts for IL-2, IL-12 p40 or IFN-gamma. Only three samples showed transcripts for both TNF-gamma and -beta, whereas four samples had transcripts for TNF-beta only, and the remaining four neither. Most samples had transcripts that indicate the presence of T-cells, both CD4 and CD8. Three samples did not show those transcripts, neither for T-cells nor for other immune system cells; some lesions in Table b showed the same pattern. It should be noted that those lesions had bands of low intensity for actin, so the signal for T cells may have been lower than the threshold of sensitivity.

Non-regressing warts grouped in Table b showed transcripts for IFN-gamma, but only two also had transcripts for IL-2. Transcripts for TNF were low for most lesions, though two samples had high levels of both. In general these lesions showed a higher grade of cytokine transcription and therefore a stronger activation of the immune system whencompared to the lesions grouped in Table a.

Non-regressing warts grouped in Table c showed transcripts for IL-12 p40, which was never present in either of the previous groups. Three lesions were negative for IL-2 and the former two were also negative for IL-2 and the former two were also negative for IFN-gamma transcripts, while the remaining lesions had transcripts for both these cytokines. Moreover TNF-alpha was present in every lesion, and was transcribed at rather high levels.

The regressing warts grouped in Table d showed a cytokine profile very similar to the one seen for the lesions in Table c: transcripts for IL-12 p40, IFN-beta and IFN-gama were present in all lesions and IL-2 transcripts were present in 4 out of 5 lesions. Normal cervix showed transcripts for IL-2. TNF and in one case for IFN-gamma, but not for IL-12 p40 (see Table e).

The examination of normal cervical tissue thus showed transcripts for IL-1beta, IL-2, IL-4, IL-8, IL-12 p35, TNF-beta, IFN-gamma and TGF-beta. IL-2 was probably due to the population of resident T sells, which has been shown to be present in normal epithelium. The presence of this population of lymphocytes was confirmed by transcripts for the cellular markers CD3, CD4 and CD8, IL-1beta, IL-4, IL-8, IL-12 p35, TNF-beta. IFN-gamma and TGF-beta could have been produced by keratinocytes or by Langerhans cells or both.

In the first group of samples there were transcripts for IL-1beta, IL-8, IL-12 p35, TNF and TGF-beta. Although there were T cells in some samples as indicated by CD3, CD4 and CD8 transcripts, no transcripts for IL-2 or IFN-gamma were detected.

In the second group of samples the pattern of cytokines was similar to that seen in normal cervical tissue with transcripts for IL-1beta, IL-8, IL-12 p35, TNF, IFN-gamma, and TGF-beta. In a few cases there were also transcripts for IL-2. This pattern seemed to suggest a more normal situation.

The samples in the third and fourth groups had very similar patterns of cytokine expression. In these lesions there were transcripts for IL-1alpha, IL-1beta, IL-2, IL-5, IL-8, IL-12 p35, IL-12 p40, TNF-alpha, TNF-beta, IFN-gamma, and TGF-beta. IL-1alpha and TNF indicate a pro-inflammatory reaction and therefore an Immune response. The most remarkable difference between these lesions and those in the previous groups seemed to lie in the presence of transcripts for IL-12 p40, which were never detectable in normal cervical tissue. IL-12 is believed to be necessary for the activation of Th1 lymphocytes and its presence therefore suggests that in these lesions the population of CD4+T cells is in the process of inducing a DTH type of response (previously reported as correlated to the clearance of the virus: S Aiba et al. 1986, Cancer 58:1246–1251). The appearance of IL-12 p40 transcripts in a small number of non-regressing lesions was believed to indicate a possibility that the patients from whom these samples were taken were in very early stage of regression but at a time when clinical improvement was not yet measurable.

The results suggest a central role of IL-12 in the local immune response to HPV infection, and raise an expectation that IL-12 is causative or adjuvant in relation to wart regression.

IL-12 PROTEIN ANALYSIS:

Biopsies of regressing and non-regressing genital warts can be analysed for expression of IL-12 and results compared. The presence of p35, p40 and the heterodimer can be examined using readily adaptable standard immunochemical technique. Antibodies recognising IL-12 are commercially available.

IL-12 protein can be detected in material taken from, regressing warts, in both keratinocytes and leukocytes. Levels of expression are higher in leukocytes, particularly dendritic cells, than in keratinocytes.

The work described herein indicates a role for IL,12 in wart regression and a link between dendritic cell expression of IL-12 and wart

EFFECT OF IL-12 ADMINISTRATION IN AN IN-VIVO MODEL:

Mouse keratinocytes expressing HPV 16 E6 or E7 or both can be grafted onto the flanks of syngeneic mice using a transplantation technique which permits reformation of a differentiated epithelium. Intradermal challenge in the ear of these animals with E7 or E6 results in a delayed type hypersensitivity (DTH) reaction. There is a relationship between the induction of DTH and the number of E7 expressing cells used to form the primary graft: there is a threshold inoculum below which although an epithelium forms no DTH is elicited, This immune non-responsiveness under these conditions is maintained on subsequent challenge and the grafted cells are not rejected. Cells are rejected in the absence of induced non-responsiveness, making this a model of HPV infection and the immune response mounted against tumours which are cause by such infection. Reference is made to C McLean et al (1993). J Gen Virol 74:239–245; M A Chambers et al (1994) Eur J Immunol 24:748–45; M A Chambers et al (1994) J Gen Virol 75:165–169; and M A Chambers et al. in 'Proceedings of the 2nd International Workshop on HPV Immunology, Cambridge UK' (July 1993) ed. MA Stanley (Plenum Press London 1994) pp267–274).

Mice can be primed with low levels of antigen by keratinocyte grafting, e.g. from less than $10^4$ to $5 \times 10^5$ keratinocytes, then given a second graft with a high inoculum, e.g $10^7$ keratinocytes. The graft is not rejected. Animals are then challenged with E7, either as a protein or encoded by and expressed from recombinant vaccinia virus.

IL-12 can be supplied to such animals with such an antigen challenge. Various routes of IL-12 supply can be readily tested, including injection of naked nucleic acid encoding it and infection with vaccinia virus able to express it from corresponding nucleic acid carried in the recombinant vaccinia-viral genome. The induction of DTH and the rejection of grafts can be used as a readout of efficiency of the protocols. Supply of IL-12 enhances the immune response mounted against the keratinocyte grafts, as evidenced by a DTH reaction. The effects of different routes of supply of IL-12 can thus be readily tested.

The invention is thus susceptible of many modifications and variations, as will be readily apparent to those skilled in the art in the light of the present description; and the present disclosure extends to combinations and subcombinations of the features mentioned shown and described herein and in the drawings and appended claims. Documents cited herein are incorporated by reference in their entire content.

What is claimed is:

1. Pharmaceutical treatment material comprising in combination (i) IL-12, or a functional homologue thereof, for use as an adjuvant, and (ii) a protein consisting essentially of at least one antigenic portion of a papillomavirus protein, wherein
   (a) the papillomavirus is selected from the group consisting of HPV types 6, 11, 16 and 18, and
   (b) the papillomavirus protein is selected from the group consisting of E6, E7, L1 and L2 proteins.

2. The pharmaceutical treatment material according to claim 1, wherein the papillomavirus protein is selected from the group consisting of E7 and L2.

3. The pharmaceutical treatment material according to claim 1, wherein the vaccine adjuvant is IL-12 or a protein that differs from IL-12 by one or more conservative amino acid substitutions and which retains IL12 activity.

4. The pharmaceutical treatment material according to claim 1, wherein the vaccine adjuvant is IL-12.

5. Pharmaceutical treatment material comprising in combination (i) IL-12, or a functional homologue thereof, for use as an adjuvant, and (ii) a nucleic acid molecule encoding a protein consisting essentially of at least one antigenic portion of a papillomavirus protein, wherein
   (a) the papillomavirus is selected from the group consisting of HPV types 6, 11, 16 and 18, and
   (b) the papillomavirus protein is selected from the group consisting of E6, E7, L1 and L2 proteins.

6. The pharmaceutical treatment material according to claim 5, wherein the papillomavirus protein is selected from the group consisting of E7 and L2.

7. The pharmaceutical treatment material according to claim 5, wherein the vaccine adjuvant is IL-12 or a protein that differs from IL-12 by one or more conservative amino acid substitutions and which retains IL12 activity.

8. The pharmaceutical treatment material according to claim 5, wherein the vaccine adjuvant is IL-12.

9. The pharmaceutical treatment material of claim 1, wherein the papillomavirus is HPV type 16.

10. The pharmaceutical treatment material of claim 1, wherein the papillomavirus protein is selected from the group consisting of E6 and E7.

11. The pharmaceutical treatment material of claim 1, wherein the papillomavirus protein is E7.

12. The pharmaceutical treatment material of claim 1, wherein the papillomavirus virus is HPV type 16 and the papillomavirus protein is E7.

13. The pharmaceutical treatment material of claim 5, wherein the papillomavirus virus is HPV type 16 and the papillomavirus protein is E7.

* * * * *

UNITED STATES PATENT AND TRADEMARK OFFICE
CERTIFICATE OF CORRECTION

Page 1 of 3

PATENT NO.    : 6,096,869
DATED         : August 1, 2000
INVENTOR(S)   : Margaret Anne Stanley, et al.

It is certified that error appears in the above-identified patent and that said Letters Patent is hereby corrected as shown below:

| | |
|---|---|
| Column 2, line 14 | "et al. J Exp Med" should read --et al., J Exp Med--. |
| Column 2, line 38 | "J Med vol 315" should read --J Med, vol 315--. |
| Column 2, line 62 | , "penis." should read --penis,--. |
| Column 3, line 24 | "IL12" should read --IL-12--. |
| Column 3, line 63 | 'Comprise" should read --comprise--. |
| Column 6, line 6 | s" should read --is--. |
| Column 6, line 17 | "con" should read --can--. |
| Column 7, line 17 | "For example. IL-12 can" should read --For example, IL-12 can-- |
| Column 7, line 33 | "cain" should read --can--. |
| Column 7, line 43 | "subunit. p35" should read --subunit, p 35,--. |
| Column 8, line 32 | "he" should read --be--. |
| Column 8, line 52 | infection," should read --infection.--. |
| Column 9, line 47 | "Transcript se" should read --Transcriptase--. |
| Column 9, line 49 | '10 mM." should read --10 mM--. |
| Column 10, line 10 | GTTT" should read --GCTTT--. |
| Column 10, line 13 | "GTCGTCGTTG" should read --GTCGTCTGTTG--. |
| Column 10, line 16 | CACGTGAA" should read --TCAGCTCGAA--. |
| Column 10, line 25 | TTAAAAA" should read --TTCAAAAA--. |
| Column 10, line 29 | IL-10 3 TCTCAGG" should read --IL-10 3' TCTCAAGG--. |
| Column 10, line 65 | GCTGAGT" should read --GCTGAAGT--. |
| Column 10, line 67 | 'CACGTC" should read --CACGTTC--. |
| Column 11, line 28 | "0.5M." should read --0.5M,--. |

UNITED STATES PATENT AND TRADEMARK OFFICE
CERTIFICATE OF CORRECTION

PATENT NO. : 6,096,869
DATED : August 1, 2000
INVENTOR(S) : Margaret Anne Stanley, et al.

It is certified that error appears in the above-identified patent and that said Letters Patent is hereby corrected as shown below:

| | |
|---|---|
| Column 11, line 29 | "pH 7.4" should read --pH 7.4--. |
| Column 11, line 42 | "CATGGGTGCTRAT" should read --CATGGGTGCTTAT--. |
| Column 11, line 44 | "IL- 1beta" should read --IL-1-beta--. |
| Column 11, line 47 | "CTTAGC" should read --CTTAAAGC--. |
| Column 11, line 49 | "IL- 5" should read --IL-5--. |
| Column 11, line 59 | "CTATT" should read --CTACTT--. |
| Column 11, line 60 | "gama" should read --gamma--. |
| Column 11, line 60 | "...AAGA" should read --AAGGA--. |
| Column 11, line 62 | "AATTAA" should read --AATTTAA--. |
| Column 11, line 67 | "0.1% v/v." should read --0.1% v/v,--. |
| Column 12, line 7 | SSCO.1x" should read --SSC O.1x--. |
| Column 12, line 9 | 150mM." should read --150mM,--. |
| Column 12, line 15 | "pH 9.5." should read --pH 9.5,--. |
| Column 12, line 17 | "NBT." should read --NBT,--. |
| Column 12, line 66 | "when-compared" should read --when compared--. |
| Column 13, line 11 | "IFN-gama" should read --IFN-gamma--. |
| Column 13, line 14 | "IL-2. TNF" should read --IL-2, TNF--. |
| Column 13, line 19 | "T sells" should read --T cells--. |
| Column 13, line 22 | "CD8, IL-1beta" should read --CD8. IL-1beta--. |
| Column 13, line 23 | "TNF beta. IFN" should read --TNF beta, IFN--. |
| Column 13, line 42 | "Immune" should read --immune--. |

UNITED STATES PATENT AND TRADEMARK OFFICE
CERTIFICATE OF CORRECTION

PATENT NO. : 6,096,869
DATED : August 1, 2000
INVENTOR(S) : Margaret Anne Stanley, et al.

It is certified that error appears in the above-identified patent and that said Letters Patent is hereby corrected as shown below:

| | |
|---|---|
| Column 13, line 51 | "et al. 1986," should read --et al., 1986,--. |
| Column 14, line 1 | 'from," should read --from--. |
| Column 14, line 7 | 'IL, 12" should read --IL-12--. |
| Column 14, line 9 | 'wart" should read --wart regression--. |
| Column 14, line 24 | "elicited," should read --elicited.--. |
| Column 14, line 31 | "(1993). J" should read --(1993) J--. |
| Column 14, line 34 | "et al. in," should read --et al., in--. |
| Column 14, line 41 | '104 to 5x105" should read --10^4 to 5x10^5--. |
| Column 14, line 43 | '107" should read --10^7--. |

Signed and Sealed this

Twenty-second Day of May, 2001

*Attest:*

NICHOLAS P. GODICI

*Attesting Officer*    Acting Director of the United States Patent and Trademark Office

UNITED STATES PATENT AND TRADEMARK OFFICE
CERTIFICATE OF CORRECTION

PATENT NO. : 6,096,869
DATED : August 1, 2000
INVENTOR(S) : Margaret Anne Stanley, et al.

It is certified that error appears in the above-identified patent and that said Letters Patent is hereby corrected as shown below:

Column 2,
Line 14, "et al. J Exp Med" should read -- et al., J Exp Med --.
Line 38, J' Med vol 315" should read -- J Med, vol 315 --.
Line 62, "penis." should read -- penis, --.

Column 3,
Line 24, "IL12" should read -- IL-12 --.
Line 63, "Comprise" should read -- comprise --.

Column 6,
Line 6, "Is" should read -- is --.
Line 17, "con" should read -- can --.

Column 7,
Line 17, "For example. IL-12 can" should read -- For example, IL-12 can --
Line 33, "cain" should read -- can --.
Line 43, "subunit. P35" should read -- subunit, p 35, --.

Column 8,
Line 32, "he" should read -- be --.
Line 52, "infection," should read -- infection. --.

Column 9,
Line 47, "Transcript se" should read -- Transcriptase --.
Line 49, "10 mM." should read -- 10 mM --.

Column 10,
Line 10, "GTTT" should read -- GCTTT --.
Line 13, "GTCGTCGTTG" should read -- GTCGTCTGTTG --.
Line 16, "TCACGTGAA" should read -- TCAGCTCGAA --.
Line 25, "TTAAAAA" should read -- TTCAAAAA --.
Line 29, "IL-10 3 TCTCAGG" should read -- IL-10 3' TCTCAAGG --.
Line 65, "GCTGAGT" should read -- GCTGAAGT --.
Line 67, "CACGTC" should read -- CACGTTC --.

UNITED STATES PATENT AND TRADEMARK OFFICE
CERTIFICATE OF CORRECTION

PATENT NO. : 6,096,869
DATED : August 1, 2000
INVENTOR(S) : Margaret Anne Stanley, et al.

It is certified that error appears in the above-identified patent and that said Letters Patent is hereby corrected as shown below:

<u>Column 11,</u>
Line 28, "0.5M." should read -- 0.5M, --.

Signed and Sealed this

Twenty-seventh Day of November, 2001

Attest:

*Attesting Officer*

NICHOLAS P. GODICI
*Acting Director of the United States Patent and Trademark Office*